US009752995B2

(12) United States Patent
Holt

(10) Patent No.: US 9,752,995 B2
(45) Date of Patent: Sep. 5, 2017

(54) CORRECTION OF SPATIAL ARTIFACTS IN RADIOGRAPHIC IMAGES

(75) Inventor: Kevin Matthew Holt, Chicago, IL (US)

(73) Assignee: Varex Imaging Corporation, Salt Lake City, UT (US)

( * ) Notice: Subject to any disclaimer, the term of this patent is extended or adjusted under 35 U.S.C. 154(b) by 1046 days.

(21) Appl. No.: 13/490,935

(22) Filed: Jun. 7, 2012

(65) Prior Publication Data
US 2013/0328919 A1 Dec. 12, 2013

(51) Int. Cl.
G09G 5/00 (2006.01)
G01N 23/04 (2006.01)

(52) U.S. Cl.
CPC ..... *G01N 23/04* (2013.01); *G01N 2223/3307* (2013.01); *G01N 2223/401* (2013.01); *G01N 2223/631* (2013.01); *G09G 2340/10* (2013.01); *G09G 2340/125* (2013.01)

(58) Field of Classification Search
CPC ........... G01N 23/04; G01N 2223/3307; G01N 2223/631; G09G 2340/125; G09G 2340/10
See application file for complete search history.

(56) References Cited

U.S. PATENT DOCUMENTS

2007/0005795 A1* 1/2007 Gonzalez ...................... 709/232
2008/0240525 A1* 10/2008 Kalke .......................... 382/128
2010/0310175 A1* 12/2010 Holt .............................. 382/195
2011/0064286 A1* 3/2011 Chien et al. ................. 382/128
2012/0328173 A1* 12/2012 Sachs et al. ................. 382/131

OTHER PUBLICATIONS

Zawadzki et al. "Correction of motion artifacts and scanning beam distortions in 3D ophthalmic optical coherence tomography imaging", Proc. of SPIE vol. 6426, 642607, (2007).*
Stephen Boyd, et al. "Distributed Optimization and Statistical Learning via the Alternating Direction Method of Amplifiers", "Foundations and Trends in Machine Learning", vol. 3, No. 1 (2010), pp. 1-122, DOI:10.1561/2200000016.
B. A. Turlach et al., "Simultaneous Variable Selection", 2005 American Statistical Association and the American Society for Quality, Technometrics, Aug. 2005, pp. 349-363, vol. 47, No. 3, U.S.A.
Jorge Nocedal, et al., "Numerical Optimization", Springer Science + Business Media, LLC, 2d ed. 2006, U.S.A. Selected readings: Chapter 1 pp. 1-9; Chapter 5 pp. 101-125; Chapter 6 pp. 135-150; Chapter 7 pp. 164-179; Chapter 11 pp. 270-275; Chapter 12 pp. 304-305; Chapter 15 pp. 421-425; Chapter 17 pp. 514-527; Chapter 18 pp. 529-535; and Chapter 19 pp. 563-569.

* cited by examiner

*Primary Examiner* — Tapas Mazumder
(74) *Attorney, Agent, or Firm* — Fitch, Even, Tabin & Flannery LLP

(57) ABSTRACT

The present invention encompasses methods, apparati, and computer-readable media for correcting spatial artifacts in composite radiographic images of an object (1). A method embodiment of the present invention comprises the steps of generating the composite image from a plurality of views of the object (1); estimating a shift profile; and re-generating the image by shifting the views using the shift profile.

26 Claims, 3 Drawing Sheets

CORRECTION OF SPATIAL ARTIFACTS IN RADIOGRAPHIC IMAGES

TECHNICAL FIELD

This invention pertains to the field of correcting spatial artifacts in radiographic images.

BACKGROUND ART

The paper "Simultaneous Variable Selection" by Turlach, Venables, and Wright, published in *Technometrics*, August 2005, Vol. 47, No. 3 (U.S.A.) (hereinafter "Reference 1"), describes a "group lasso" method that can be used in the present invention. *Numerical Optimization* by Nocedal and Wright (2d ed. 2006), published by Springer Science+Business Media, LLC, describes, at Chapters 1, 5-7, 11, 12, and 17-19, methods that can be used in the present invention (hereinafter "Reference 2").

The present inventive method is somewhat similar to non-rigid registration methods (commonly used in medical imaging) that register two images against each other; however, the present method takes no reference image. It registers the image against itself to find a smooth output image that is similar to the input image. No known prior art geometrically unbends an image in this way without having a reference image to compare to.

DISCLOSURE OF INVENTION

The present invention encompasses methods, apparati, and computer-readable media for correcting spatial artifacts in composite radiographic images of an object (1). A method embodiment of the present invention comprises the steps of generating the composite image from a plurality of views of the object (1); estimating a shift profile; and re-generating the image by shifting the views using the shift profile.

BRIEF DESCRIPTION OF THE DRAWINGS

These and other more detailed and specific objects and features of the present invention are more fully disclosed in the following specification, reference being had to the accompanying drawings, in which.

DETAILED DESCRIPTION OF PREFERRED EMBODIMENTS

Figure 1:
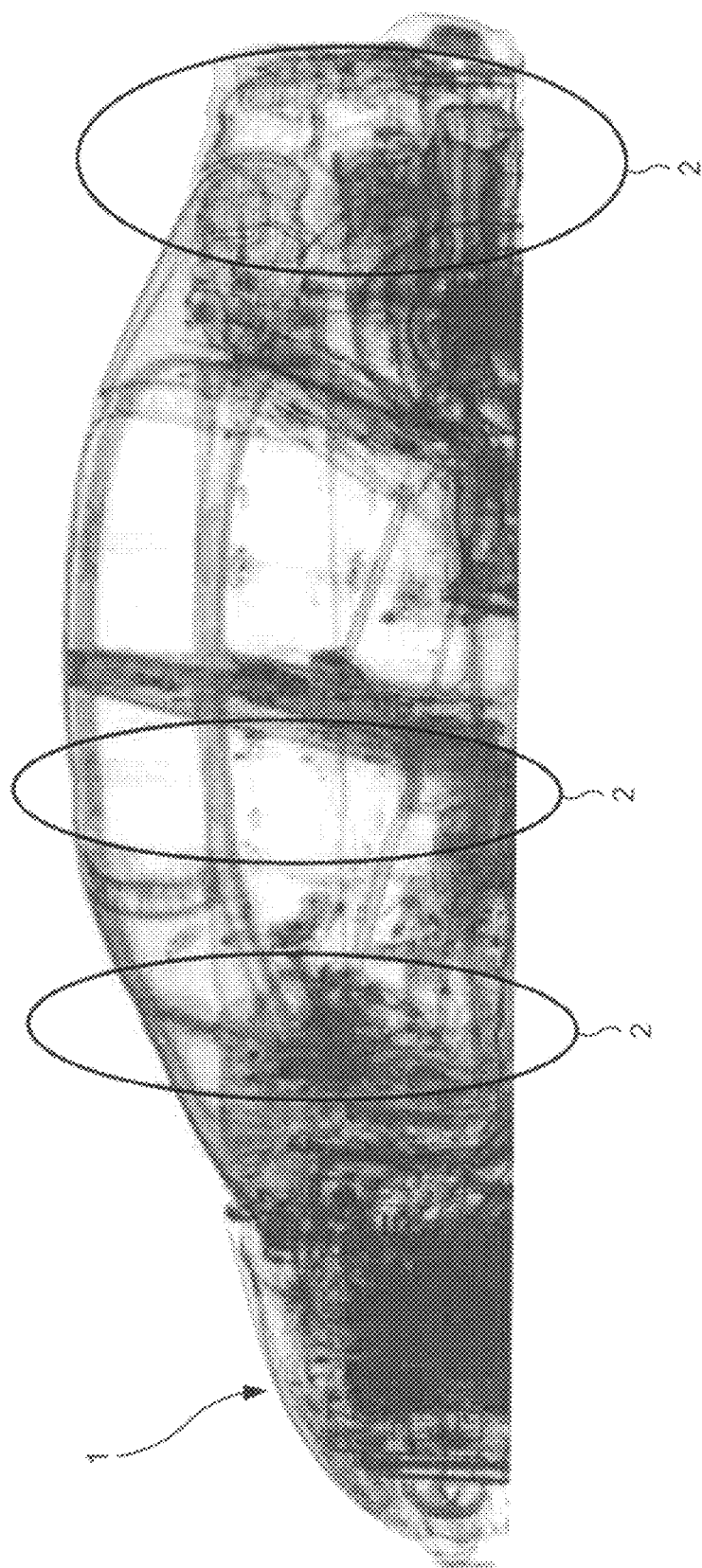
FIG. 1 is a prior art composite radiograph of an automobile 1 made by taking several views of the automobile 1 by an x-ray scanner that is at relative motion with respect to the automobile 1.

This invention comprises methods to correct spatial artifacts in a composite radiograph. In the embodiment illustrated herein, the spatial artifact is a wiggle 2 that appears along one direction; the composite radiograph comprises a plurality of views of an object 1; and each view is one pixel wide in the horizontal direction and many pixels tall in the vertical direction (enough pixels tall to cover the entire height of the object 1). It is important to note that, while the view in the illustrated embodiment is one pixel wide, this invention is fully viable when the view is more than one pixel wide.

As used herein, "radiograph" means any two-dimensional image, such as an image made by radiography, a camera, magnetic resonance imaging device, computerized tomographic device, etc.

An object 1 is scanned by a scanner by causing relative motion between the object 1 and scanner, generally either by moving the object 1 through a stationary scanner, or by moving the scanner or its imaging beam with respect to a stationary object. Image frames (called views) are acquired sequentially as the object 1 is scanned, resulting in a collection of multiple (usually many) image views. These views are then typically assembled into some composite image, such as in the form of a 2D image or radiograph, or as a tomographic reconstruction.

If any of the motions are confounded by non-ideal mechanics, artifacts can result. One important example is when the object 1 is passed through the scanner using a conveyor system or towing system, such as for cargo or vehicle security inspection, or for industrial non-destructive testing. If there are any bumps, gaps, or dips in the conveyor or in the chamber floor, or any jerks in the towing system, the object 1 can shift in ways that can cause artifacts. The problem can also be confounded when the object 1 itself is further prone to bouncing. For example, when the object 1 is a car (or other vehicle), not only does the initial insult create an artifact, but the car's suspension may continue to bounce for some time after the insult, which can result in a wiggle artifact 2 in the radiograph, or even more severe artifacts in tomographic reconstruction.

In the example illustrated herein, object 1 is an automobile moving along a conveyor, and the radiographic imaging is performed by two fixed x-ray imaging chains (one imaging the car 1 from a vertical perspective and one imaging the car 1 from a horizontal perspective). There is relative motion between the object 1 being imaged and the imager. Alternatively to the car 1 moving along a conveyor, car 1 could be towed through the imaging chamber. In alternative embodiments, the object 1 being imaged is stationary and the scanner moves past the object 1 within a moving gantry. The motive for imaging the car 1 can be to detect contraband materials, such as weapons, drugs, etc., that may be hidden within the car 1. In the illustrated embodiment, imaging is performed in a horizontal direction by an imaging chain with its source positioned on one side of the car 1, with an associated detector array positioned on the opposite side of the car 1. The radiographic images depicted in the three Figures are from the imaging that is performed in the horizontal direction by the x-ray scanner.

When imaging at modest energies (several keV to several hundred keV), it is practical (and common) to build area detectors that are both many pixels tall and many pixels wide. However, at higher energies (several MeV), it is generally more common to make detectors that are only one or two pixels wide, since this allows the electronics to be well-shielded from damaging radiation in a cost-effective way. In the illustrated example, the x-ray detector associated with the horizontal x-ray imager is many pixels tall, but only one pixel wide. As a result of this, many views of the car 1 are taken to build up the composite radiographic images that are depicted in the Figures, one column at a time.

In the illustrated example, the scanner also has a second imaging chain with its x-ray source positioned above the passageway through which the car 1 moves, and its x-ray detector positioned below the passageway. This second imaging chain gives a second perspective which enhances the odds of detecting things hidden in the car 1 (or other scan object). Furthermore, in this example, the conveyor system is arranged as two different conveyor belt sections with a gap in between them, designed so that the second imaging chain's x-rays pass through this gap without imaging the conveyor (which could otherwise create artifacts). However, the car 1 may experience a dip or bump as it reaches this conveyor gap. From the point of view of the side x-ray scanner, this causes the car 1 to bounce vertically when the car 1 hits conveyor discontinuities. Since the car 1 is being imaged as it is bouncing, the views are affected (mostly shifted up and down) relative to each other as the car 1 moves along the conveyor, producing a series of vertical spatial artifacts (wiggles) 2, as shown in FIG. 1. While in this example, the wiggles 2 are caused by a gap in a conveyor that is introduced to accommodate a top-view imaging chain, similar wiggles could occur for other reasons and/or in other types of scanners, including scanners that are side-view only.

The present invention corrects for the spatial artifacts 2 using methods that are fully automatic, with no (or minimal) user interaction.

The methods are described as follows:

Let t be time.

Let k be view number. Usually (but not necessarily), views are sampled at a constant sample rate, so $t=k \times \Delta t$ Let x be horizontal position relative to some reference point on the car 1. If the conveyor is moving at constant speed, $x=vel \times t$ where vel is velocity.

The correction is described by a shift profile, which we can think of continuously: $s(t)$, or discretely: $s[k]$.

The method has two main portions:
1) Estimate $s[k]$ (shift profile estimation step)
2) Re-generate the image by shifting each view by $s[k]$ The second step can be accomplished by any interpolation strategy, such as bilinear, cubic, B-spline, or sinc interpolation (including truncated sinc interpolation, or FFT-based sinc interpolation). The first step (shift profile estimation) is more complicated. We can optionally apply a simple smoothing filter to $s[k]$ between steps 1 and 2, though a good step 1 usually requires no post-filter.

Shift profile estimation can be accomplished through an optimization method, where we specify several criteria, and the method searches for a solution automatically. A very general form for specifying such problems is:

Find $s$ to minimize $\lambda_1 f_1(s) + \lambda_2 f_2(s) + \lambda_3 f_3(s) + \ldots$ such that
[constraint 1] is true, and
[constraint 2] is true, and
[constraint 3] is true, and . . .
where the $\lambda$'s are weights and the f's are penalty functions. $\lambda_i$ can be thought of as representing the importance of minimizing $f_i$ relative to the other penalties. The constraints are typically equalities or inequalities involving additional functions of s. We will refer to this form as an "optimization problem".

We can use many methods for solving general problems in this form. Specific options are described below.

We now describe several criteria (choices of f and/or constraints). There are two main classes of criteria. In general, we need at least one criterion from each class.

Shift Criteria

The first class of criteria governs $s[k]$. We know that a damped spring typically has an impulse response proportional to $e^{-\alpha t} \cos(2\pi f_o t)$ for $t>0$, where $\alpha$ is a damping factor, and $f_o$ is a fundamental frequency (usually between 1 Hz and 2.5 Hz for a typical car 1 suspension). Therefore, if the car 1 receives a jolt of size A at time $t_o$, we can expect the following conditions to be satisfied:

$|s(t)| \leq A$ for all $t$ $|s'(t)| \leq A\sqrt{(2\pi f_o)^2 + \alpha^2}$, for all $t > t_o$, where $s'$ is the derivative of $s$ $|s''(t)| \leq A((2\pi f_o)^2 + \alpha^2)$, for all $t > t_o$, where $s''$ is the $2^{nd}$ derivative of $s$

. . .

$|s^{(n)}(t)| \leq A((2\pi f_o)^2 + \alpha^2)^{n/2}$, for all $t > t_o$, where $s^{(n)}$ is the $n$'th derivative of $s$.

Note that $t_o$ is the time of the insult (i.e., the time when the wiggle 2 starts, such as the time when the car 1 hits the bump in the conveyor).

The following are three ways to enforce that these conditions become true (either approximately or exactly) for our calculated s:

Option 1)

We can enforce these conditions directly as [constraint 1], [constraint 2], etc by using finite differences. First, estimate the largest reasonable values of A, $f_o$, and $\alpha$, and call these $A_{max}$, $f_o^{max}$ and $\alpha_{max}$.

For equally spaced views, the constraints become, in continuous time $|s(t)| \leq A_{max}$, for all $t$ $|s'(t)| \leq A_{max}\sqrt{(2\pi f_o^{max})^2 + \alpha_{max}^2}$ for all $t > t_o$ $|s''(t)| \leq A_{max}((2\pi f_o^{max})^2 + \alpha_{max}^2)$ for all $t > t_o$

. . .

or in discrete time (which is easier to enforce and thus the preferred method), by using finite differences:

$|s[k]| \leq A_{max}$ for all $k$ $|s[k+1] - s[k]| \leq A_{max} \Delta t \sqrt{(2\pi f_o^{max})^2 + \alpha_{max}^2}$ for all $k \geq k_o$ $|2s[k+1] - s[k] - s[k+2]| A_{max} \Delta t^2 ((2\pi f_o^{max})^2 + \alpha_{max}^2)$, for all $k \geq k_o$

. . .

The insult view-number, $k_o$, can either be explicitly estimated, or we can just replace "for all $k > k_o$" with "for almost all k". In the latter case, in other words we can forget about $k_o$ and essentially enforce the constraint for all k, but use a method that enforces the constraint for the most part but allows a small number of isolated violations.

Option 2)

Alternatively, we can simply encourage these derivatives to be small, using penalty functions $$f_1 = \sum_k \psi_1(s[k])$$

$$f_2 = \sum_k \psi_2(s[k] - s[k-1])$$

-continued $$f_3 = \sum_k \psi_3(2s[k] - s[k-1] - s[k+1])$$

...

where $\psi$ is some penalty function.

A straightforward choice is squared error, $\psi(z)=z^2$

Another choice is absolute error, $\psi(z)=|z|$. This can lead to an optimization problem that can be hard to solve, but gives less weight to large outliers, which is desirable. For instance, s' and s" might be large at $t_o$ but small everywhere else, and this choice can lead to an answer that is relatively unaffected by the data at $t_o$, even without explicitly estimating the time $t_o$ (or $k_o$).

Another choice, a compromise between the above two, is the Huber function, $$\psi(z) = \begin{cases} z^2, & |z| \le \delta \\ \delta \times (2|z| - \delta), & |z| > \delta, \end{cases}$$

where a good choice for the n'th derivative is $\delta = A_{max} \Delta t^n ((2\pi f_o^{max})^2 + \alpha_{max}^2)^{n/2}$. This again gives less weight to large outliers, but for smaller non-outliers behaves like squared-error (which can give more accurate answers than absolute error).

Option 3)

The Fourier transform of s should be small above the fundamental frequency of the spring. Let $F_j s$ denote the j'th frequency bin of the Fourier transform of s. Let $j_o$ be the bin above which we think there is no high frequency information (i.e., $j_o$ is the bin corresponding to $f_o^{max}$, or slightly above it). Then we can assert a hard constraint on each high frequency component, $|F_j s| \le \delta_j$ for all $j \ge j_o$, or we can assert a hard constraint on the total high-frequency content, $$\sum_{j \ge j_o} |F_j s|^\gamma \le \delta$$

where a good choice for $\gamma$ is 2 or 1.

The thresholds are any $\epsilon \ge 0$. Note that $\epsilon = 0$ is a perfectly valid choice, which says that there should be zero high frequency energy in the shift signal, which is appropriate if the bounce is band-limited. However, since the initial jolt might have high frequency components, a more appropriate choice is to calculate $\epsilon$ from the energy due to an initial impulse of height $A_{max}$.

Option 4)

The Fourier transform can also be penalized in a soft way by using a penalty function $$f(s) = \sum_j \psi_j(F_j s)$$

where $\psi$ is one of the choices presented above, and could even be different for different frequency bins.

In options 3 and 4, one can use transforms other than the Fourier transform. For example, one could use a Discrete Cosine Transform (DCT) or wavelets.

Option 5)

Group sparsity. We might assume that s=0 for most times, except for within a couple of small windows (i.e., groups of times or views). This is particularly true when α is large. Say that we create M different windows, where window m runs from $k_m^{start}$ to $k_m^{end}$. Then we can penalize:

$$f(s) = \sum_m w_m \left( \sum_{k_m^{start}}^{k_m^{end}} s[k]^2 \right)^{1/2}$$

$$\text{or } f(s) = \sum_m w_m \times \max_{k_m^{start} \le k \le k_m^{end}} |s[k]|.$$

These choices correspond to the penalties in the "group lasso" method. Reference 1, supra.

We add the extra weighting term $w_m$, which penalizes different windows differently. For example, bigger windows could be penalized more than smaller windows, or vice versa. Or windows could be penalized more when they are not expected to contain a bounce.

Image Criteria

The second class of criteria governs that the re-generated image is relatively free of wiggles 2. We give three general methods for doing this: Option 1)

Perform an edge detection on the image. Say we have found N edges. Then each edge $E_N$ is a list of (x,y) points. We want to encourage this edge to be smooth in the re-generated image, by penalizing $$f_1(s) = \sum_i w_i \sum_{(x,y) \in E_i} \psi_1\left(\frac{d(y-s)}{dx}\right),$$

$$f_2(s) = \sum_i w_i \sum_{(x,y) \in E_i} \psi_2\left(\frac{d^2(y-s)}{dx^2}\right)$$

...

Figure 2:
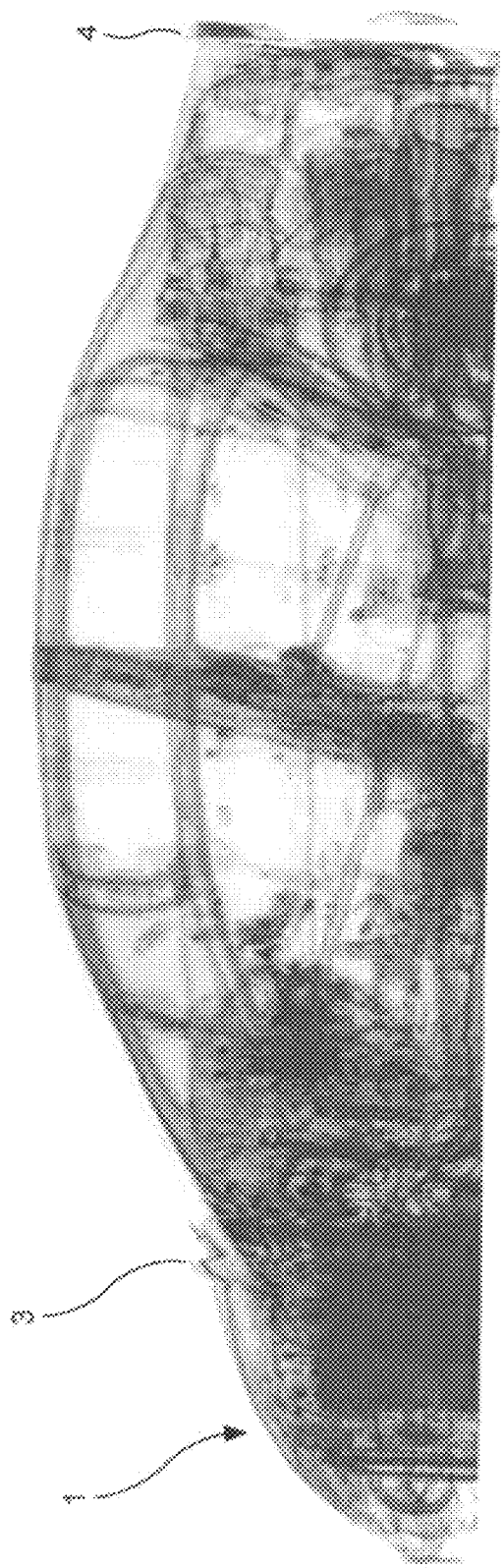
FIG. 2 is the radiograph of the automobile 1 of FIG. 1 for which option 2 of a shift criterion and option 1 of an image criterion has been performed using techniques of the present invention.

Note that the y profile is measured (known), and the s profile is unknown (to be estimated). The first penalty function, $f_1$, encourages a small first derivative, which encourages edges to form horizontal lines. The second penalty function encourages a small second derivative, which encourages straight (though not necessarily horizontal) lines. An optional third penalty function could encourage small second derivatives, which would encourage edges to follow curves that are smooth (though not necessarily straight lines) with no kinks. Even higher orders are possible. One can use a single one of these penalty functions by itself, or multiple penalty functions, by adding them together. This method is sensitive to errors in edge estimate. For example, FIG. 2 shows an example of this method where we find a single edge—the top edge of the car 1, and the method has some trouble. Note that in this example, we have smoothed out the original wiggles 2, but accidentally introduced new ones 3, 4 where we traced the car 1 edge non-optimally. So this method requires very accurate edge tracing (in which case the method can work well).

Option 2)

Calculate a displacement field d[k], which measures an estimated shift between neighboring image frames. The preferred method for this is:

Let P(k, . . . ) be the image frame for view k, which can be either 1D (as in the case where the detector is a single column) or a 2D image (as in the case where the detector is an area detector such as a flat panel detector, image intensifier, CCD, or 2D crystal array). This frame data will typically be processed with standard preprocessing steps known in the art such as electronic offset subtraction, air normalization, and correction for source fluctuations. Preprocessing may also include resampling, in which case the data coordinates described in this invention are with respect to the resampled coordinate space. Let P(k,i,j) be the pixel value for the pixel with coordinates (i,j) from image frame k. For example, in the case where the detector is vertical and a single pixel wide, and the image frames are concatenated horizontally to form a radiograph, k is horizontal index (i.e., view) within the radiograph, i is vertical index (i.e., channel number), and j is unused so we can just treat it as j=1.

Let $Q_v(k,i,j)=P(k,i-v,j)$. i.e., Q is a frame of P, shifted by some amount v (the shift is vertical in our example). Note that in general, v may not be an integer, so some interpolation is usually required. This can be any of the methods allowed in Part 2 of the main algorithm (bilinear, cubic, B-spline, sinc, etc.), but need not be the same method as in Part 2.

Then let the displacement d be $$d[k] = \operatorname*{argmax}_v \Phi_{sim}(P(k, \ldots); Q_v(k+1, \ldots)), \text{ or}$$

$$d[k] = \operatorname*{argmin}_v \Phi_{diff}(P(k, \ldots); Q_v(k+1, \ldots))$$

where $\Phi$ is some similarity measure ($\Phi_{sim}$ equation) or difference measure ($\Phi_{diff}$ equation). Therefore, if we shift two neighboring views (i.e., frames) by different amounts, d[k] is the shift that makes views (k) and (k+1) the most similar.

Some choices for $\Phi$ include:

$$\Phi_{diff}(p, q) = \sum_{i,j} \psi(p(i, j) - q(i, j))$$

where $\psi$ is any penalty function mentioned above, or $\Phi_{sim}(p,q)$=the mutual information between p and q (it is known in the art how to calculate this)

$\Phi_{sim}(p,q)$=the normalized mutual information between p and q (it is known in the art how to calculate this)

$\Phi_{sim}(p,q)$=the structural similarity between p and q (it is known in the art how to calculate this)

It can be useful to mask out any air pixels, bad pixels, pixels through very long (impenetrable) paths, or any other pixels that can be asserted to not provide any useful information, prior to the calculation of $\Phi$.

Now say that some image feature (such as an edge, a ridge, or a texture) follows a shape trajectory y(x), which describes the natural shape of the object in the same direction as the shift we are trying to measure. In this example, since we are measuring vertical shift, the shape trajectory is naturally described by vertical location as a function of horizontal location. However, since horizontal location corresponds to time, for any y(x) there is an equivalent time-based trajectory y(t). In the measured image, which is subject to the unknown shift s(t), a feature with shape trajectory y(t) would appear to have an observed trajectory y(t)+s(t). Typically, there are many such points that all behave this way. Furthermore, d is essentially the estimated derivative of this observed trajectory, so d(t)≈y'(t)+s'(t).

Essentially, our goal is to estimate s from d, without knowing y. This is one equation with two unknowns, which by conventional wisdom cannot be solved. However, we can use prior knowledge of both s and y to make a solution possible. In Part 1, the shift criteria class described criteria that encourage s to be physically likely. Now in Part 2, we describe criteria that encourage y to be physically likely.

For many objects 1, including most cars or trucks, we observe that y(t) usually changes continuously (even smoothly, for much of the image). We can therefore design penalty functions to specifically encourage solutions that are consistent with reasonable y profiles.

This leads to the following penalty functions:

$$f_1(s) = \sum_k w_k \psi_1(d[k] - s'[k])$$

$$f_2(s) = \sum_k w_k \psi_2(d'[k] - s''[k])$$

$$f_3(s) = \sum_k w_k \psi_3(d''[k] - s'''[k])$$

...

where the derivatives are implemented as finite-differences shown above, and $w_k$ is a weight that measures how accurately we think s has been measured for a given view. While $\phi$ could be a simple form like squared error, often it is much more powerful to choose $\phi$ as a function such as absolute error, or the Huber function, that is more robust to outliers. This can be important for two reasons. The first reason is that d includes measurement error, and ideally we would like to be tolerant to an occasional significantly wrong value of d. The second reason is that while y is usually smooth, there may be large discontinuities at some points, for example at the back of the cab in a truck. Since such discontinuities can create large derivatives of y, it can be beneficial to treat such large values as outliers (i.e., we would like the derivatives of y to be small at most points, but it is fine if the derivatives of y are very large in just a few places).

The first of the penalty functions listed above, $f_1$, essentially says that y'(t) should usually be close to zero, or in other words, that object features should usually follow a horizontal trajectory (i.e., most edges are horizontal). The second essentially says that y''(t) should usually be close to zero, or in other words, that object features should usually follow a straight line (at any angle), with relatively few bends in them. The third essentially says that the third derivative of y(t) should usually be close to zero, or in other words, the object 1 features should usually follow smooth curves, but the amount of curvature does not usually change much from view to view. And so forth. One might use a single one of these penalties by itself, or several of these, by adding them together.

The weights $w_k$ can be measured in several ways. For example, they can be measured by measuring the curvature of $\Phi$ about d[k], where curvature is the second derivative of $\Phi$ with respect to v. If it has high curvature, the extreme value d[k] is well defined and has high confidence. If it has low curvature, many values give similar similarities/differences, and therefore we have low confidence in our measured value of d[k].

The weights can also be measured (either instead of or in combination with curvature) by measuring the difference or similarity value. If the two frames of P even after shifting are not sufficiently similar, or if they do not have sufficiently small difference, we have little confidence in d[k].

The weights can also be measured (again, either instead of or in combination with the above) by measuring the magnitude of d[k] or d'[k]. When either of these are exceptionally large, we can assume that that d[k] measurement is probably unreliable, and therefore decrease its confidence.

This option can also be applied in patches. That is, rather than measuring a single d[k] for each frame, we can measure it for several vertical patches, d[k,j], for several values of j, each corresponding to a different (though possibly overlapping) patch of pixels. These might be, say, 20 or 50 pixels tall. Each patch gets its own weight. Then we have the penalties:

$$f_1(s) = \sum_{k,j} w_{k,j} \psi_1(d[k, j] - s'[k, j])$$

$$f_2(s) = \sum_{k,j} w_{k,j} \psi_2(d'[k, j] - s''[k, j])$$

...

We can optionally smooth or filter d (say, to remove outliers) prior to applying the above penalties.

Option 3)

The corrected image should itself be smooth. Let P and Q be defined as above.

A simple criterion is that the total energy in the gradient of the corrected image should be small:

$$f(s) = \sum_{k,j} \left( \left( \frac{d}{dk} Q_{s[k]}[k, j] \right)^2 + \left( \frac{d}{dj} Q_{s[k]}[k, j] \right)^2 \right)$$

However, this may not allow for hard edges or outliers. Another alternative is the Total Variation (TV) semi-norm, $$f(s) = \sum_{k,j} \sqrt{ \left( \frac{d}{dk} Q_{s[k]}[k, j] \right)^2 + \left( \frac{d}{dj} Q_{s[k]}[k, j] \right)^2 }$$

These can be generalized to also include other options such as the Huber function. One possibility is:

$$f(s) = \sum_{k,j} \psi \left( \sqrt{ \left( \frac{d}{dk} Q_{s[k]}[k, j] \right)^2 + \left( \frac{d}{dj} Q_{s[k]}[k, j] \right)^2 } \right)$$

Note that the vertical derivative of Q is independent of shift amount. Thus, the second squared term in each of the above equations may be precalculated once and stored. Alternatively, it could also be omitted altogether, yielding:

$$f(s) = \sum_{k,j} \psi \left( \frac{d}{dk} Q_{s[k]}[k, j] \right)$$

This gives different results, but can still be useful.

In order to calculate $$\frac{d}{dk} Q_{s[k]}[k, j],$$

note when we write $Q_v(k,i) = P(k, i-v)$, this is actually shorthand for an interpolation, which can be written:

$$Q_{s[k]}(k, i) = \sum_{m,n} \Lambda(k - m, i - s(k) - n) P(m, n)$$

where $\Lambda$ is an interpolation kernel. Then:

$$\frac{d}{dk} Q_s(k, i) =$$

$$\sum_{m,n} P(m, n) \times (\Lambda'_{(a)}(k - m, i - s[k] - n) - \Lambda'_{(b)}(k - m, i - s[k] - n) s'[k])$$

where $\Lambda'_{(a)}$ and $\Lambda'_{(b)}$ are the derivatives of $\Lambda$ with respect to its first and second arguments, respectively, and s'[k] can be approximated by $$\frac{d}{ds} s[k] = (s[k + 1] - s[k - 1])/2.$$

or symmetrically by $$\frac{d}{ds} s[k] = s[k + 1] - s[k]$$

View-Chunk Selection

While the above methods can be used to process an entire image at once, it can also be more efficient to separately process smaller chunks of the data. For example, in FIG. 1, the only artifacts to be corrected are in the circled regions 2. For the remainder of the views, we can assume that s[k]=0, so we can save computations by removing these views from the optimization problem.

One method to choose which views to process is to analyze the image to directly look for the presence of artifacts. Another method is to identify a feature in the object that is linked to the location of the artifacts. For example, in a car, the bounce artifact typically starts some fixed number of views relative to the location of the wheel. Thus, in one embodiment of this invention:

Parameters offset(n) and length(n) define the location and size of a window relative to the location of wheel #n. For a car, n=1 to 2 (for front and back wheels, respectively).

For each n, identify the views $k_{wheel}(n)$ corresponding to wheel #n.

Create n different windows, each going from view $k_{wheel}(n)$+offset(n) to view $k_{wheel}(n)$+offset(n)+length(n).

Merge any windows that overlap

Process each window independently, using the techniques described above.

The step of identifying the wheel locations $k_{wheel}(n)$ can itself be done in several ways:

By a mechanical sensor (if available).

By analyzing the side-view image, such as by identifying the axle location, or looking for a tire extending below the vehicle.

By analyzing the top-view image (if available). In some cases, the wheels are supported by a pusher-arm system. These arms can easily be identified by computer vision algorithms, which in turn tells us the wheel locations.

These can be combined. The preferred method is: If a mechanical sensor is present, use that. Otherwise, if the system has a top-view and there are pusher arms and the pusher arms can be confidently identified, use those. Otherwise, if the wheels can be confidently located in the side-view, use those locations. Otherwise, process the entire data set (i.e., use a single processing window that spans the entire car).

Multi-Dimensional Data

While many scanners produce single-dimensional data (i.e., data using a single source spectrum and a detector with no energy selectivity), scanners that produce higher-dimensional data are becoming increasingly common, by using multiple-energy sources (such as a dual-energy Linatron), energy-selective detectors (such as multi-layer detectors or energy-discriminating photon counting detectors), or multiple imaging modalities (such as both X-rays and MRI). In all of these cases, we are typically presented with multiple images (or a single image with vector-valued pixels) of the same object with different physics imaging.

Some scanners that produce multi-dimensional data obtain the multiple dimensions by using multiple passes. That is, the data is scanned once to obtain one dimension, again to obtain another dimension, and so forth. In this case, if any of these passes contain artifacts, the algorithm presented here can be used on each pass independently, since the bounce artifacts might be different for the different passes.

Scanners can also produce multi-dimensional data concurrently where several dimensions are acquired at once, for example by using energy-selective detectors, or X-ray sources with interlaced energies. In this case, since each dimension is acquired at the same time, each dimension should contain the same artifact. Thus, in this case it is preferred to estimate a single common shift profile that is independent of imaging dimension. This can be performed by using only a single dimension to measure the shift profile, then applying it to all dimensions. For example, for dual-energy X-ray imaging, we can measure s[k] from the high-energy image, but then use this same s[k] for both the high-energy and low-energy data for the step of re-generating the image by shifting the views using the shift profile. Alternatively, we can use more than one dimension to estimate s[k]. For example, for dual-energy X-ray imaging, we can measure displacement fields for both the high-energy and low-energy images, then augment our penalty function to encourage a single shift profile s to be consistent with both the high- and low-energy displacement fields. For example, we can use the penalty function $$f(s) = \sum_k w_k^{hi} \psi(d_{hi}[k] - s'[k]) + \sum_k w_k^{lo} \psi(d_{lo}[k] - s'[k]).$$

where $d_{hi}$ and $d_{lo}$ are the displacement fields respectively measured from the high- and low-energy images.

Some scanners might both collect some dimensions concurrently, and some dimensions through multiple passes. The above techniques can be combined to accommodate this case.

Solving

There are many available methods and algorithms for solving problems such as the ones presented in this specification. Generally, these come in the form of an algorithm description (i.e., a book, paper, or Web page), which can be implemented in custom software, or in the form of third party software, which in turn might implement either published methods or proprietary methods.

The methods themselves come in categories. One category of optimization method uses gradients—these include steepest descent, nonlinear conjugate gradient methods, trust-region methods, BFGS, L-BFGS, other Newton or quasi-Newton methods, or many of the methods from Reference 2, supra. These generally work well for squared error terms and often Huber functions, but can have difficulty with anything that is non-differentiable, including L1 norms (i.e., absolute error), the group sparsity terms listed above, or Total-Variation. One solution is to modify the penalties to make them differentiable. Another solution is to use a second class of algorithm that does not explicitly rely on gradients—this includes proximal mappings, the ADMM method, the parallel proximal algorithm, iterative shrinkage, subgradient methods, or similar methods (there are many) which natively handle non-differentiable costs. A third class of methods is frequently called "derivative free optimization" and includes methods such as pattern-search, the nelder-mead method, simulated annealing, or genetic algorithms. This class is usually slower than the other methods, so the other classes are generally preferable.

Yet another class of methods is commonly referred to as "convex programming", which typically uses one or more of the above methods together inside a larger framework designed to handle constraints and non-differentiability, though some methods give solutions where the constraints are always satisfied exactly, while some give solutions where the constraints are satisfied only approximately. This class of methods includes interior point methods, linear programming, quadratic programming, and augmented Lagrangian methods. They are often quite efficient, and require only that all functions and constraints are convex. Conveniently, most of the options presented above are convex, so we can often use a convex solver.

In the scope of this invention, any of these methods could be implemented in custom software. Alternatively, there are many third party software codes available to solve problems specified in the general form mentioned in this specification. Applicable third party solver codes include CVX or Yalmip (both of which rely internally on more specialized solvers such as SDPT3 or Sedumi), or more commercial solvers such as Knitro, Mosek, or CPLEX.

EXAMPLE

Figure 3:
FIG. 3 is the radiograph of the automobile 1 of FIG. 1 for which option 2 of a shift criterion and option 2 of an image criterion of the present invention have been performed.

FIG. 3 is an image made by using the following penalties (with no hard constraints):
  Shift criterion, option 2
    Total energy in s, f=sum(s$^2$), and
    Total energy in s', f=sum((s')$^2$), and
    Total energy in s", f=sum((s")$^2$)
  Image criterion, option 2
    Total energy in (d–s'), f=sum(|d–s'|), and
    Absolute error of (d'–s"), f=sum(|d–s"|)
    s weighted to reject values where d' is large or curvature is small.

The method steps in the aforesaid description are typically performed by modules. The modules can be embodied in any combination of hardware, firmware, and/or software. When embodied in software, the modules can reside on one or more computer-readable media such as hard disks, floppy disks, optical drives, DVD's, thumb drives, etc.

The above description is included to illustrate the operation of the preferred embodiments, and is not meant to limit the scope of the invention. The scope of the invention is to be limited only by the following claims. From the above discussion, many variations will be apparent to one skilled in the art that would yet be encompassed by the spirit and scope of the present invention.

What is claimed is:

1. A method for correcting spatial artifacts within a composite radiographic image of an object, said method comprising the steps of:
generating the composite image by assembling a plurality of views of the object imaged by a radiographic scanner, wherein each view represents a different time, relative motion exists between the radiographic scanner and the object, and each view corresponds to a portion of data used to generate the composite image and where each view is no more than two pixels wide in a horizontal direction and many pixels tall in a vertical direction to cover entire height of the object;
estimating a correctional shift profile comprising tailored correctional shifts for at least two of the views;
correcting the views using the corresponding correctional shifts; and
re-generating the image by assembling the corrected views.

2. The method of claim 1 wherein the correctional shift profile is represented by s[k], where k is a view number representing a time when the corresponding view was obtained.

3. The method of claim 1 further comprising performing, between the estimating step and the re-generating step, the step of applying a smoothing filter to the correctional shift profile.

4. The method of claim 1 wherein the re-generating step is accomplished by interpolation.

5. The method of claim 4 wherein the interpolation is from the group of interpolations consisting of bi-linear, cubic B-spline, and sinc.

6. The method of claim 1 wherein the step of estimating a correctional shift profile utilizes an optimization algorithm.

7. The method of claim 1 wherein the composite radiographic image is produced by x-rays.

8. The method of claim 1 wherein each view is one pixel wide and many pixels tall, the re-generating step comprises concatenating corrected views, and the concatenation is performed horizontally.

9. The method of claim 1 wherein more than one image is re-generated using the same correctional shift profile.

10. The method of claim 1 wherein fewer than all of the views are corrected.

11. The method of claim 10 comprising the following steps:
examining the image to identify one or more artifact-related features;
identifying one or more subsets of views relative to locations of the artifact-related feature(s); and
correcting only the identified subset(s) of views.

12. The method of claim 11 where the artifact-related features are wheels on a car or truck.

13. The method of claim 1 wherein the step of re-generating the image comprises concatenating the corrected views.

14. The method of claim 1 wherein the composite image is a two dimensional (2D) image, and each view is a portion of the 2D image.

15. The method of claim 1 wherein the correctional shifts correct a spatial artifact, and the spatial artifact is a wiggle that appears along one direction.

16. A method for correcting spatial artifacts within a composite radiographic image of an object, said method comprising the steps of:
generating the composite image by assembling a plurality of views of the object imaged by a radiographic scanner, wherein each view represents a different time, relative motion exists between the radiographic scanner and the object, and each view corresponds to a portion of data used to generate the composite image;
estimating a correctional shift profile comprising tailored correctional shifts for at least two of the views;
correcting the views using the corresponding correctional shifts; and
re-generating the image by assembling the corrected views;
wherein the step of estimating a correctional shift profile utilizes an optimization algorithm; and
the optimization algorithm is applied to find the correctional shift profile that minimizes a sum of a set of penalty functions such that the optimization algorithm at least approximately satisfies a set of hard constraints, wherein each hard constraint uses a Fourier transform to constrain high frequency components of the shift profile to be within a preselected value.

17. The method of claim 16 wherein the penalty function(s) comprise(s) at least one function from the group consisting of a squared error function, an absolute error function, and a Huber function.

18. The method of claim 16 wherein:
each penalty function and each constraint is from one of two classes of criteria: a shift criterion class and an image criterion class;
the shift criterion class governs the shift profile expressed as a discrete function of time;
the image criterion class governs that the re-generated image is relatively free of wiggles; and
criteria from both classes are employed by the optimization algorithm.

19. The method of claim 18, wherein each class is represented by at least one penalty function or constraint.

20. The method of claim 18 wherein the shift criterion class is enforced by at least one step from the following:
using finite differences;
encouraging derivatives of the shift profile to be small;
hard penalizing a Fourier or other transform;
soft penalizing a Fourier or other transform;
using group sparsity.

21. The method of claim 18 wherein the image criterion class is satisfied by at least one step from the following:
performing an edge detection on the image, producing a corrected image, and encouraging edges in the corrected image to have a desired shape;
calculating a displacement field and encouraging some component of the shift profile to be similar to the displacement field;
encouraging the corrected image to be smooth.

22. The method of claim 21 wherein the step of encouraging the corrected image to be smooth comprises at least one of:
encouraging total energy in the gradient of the corrected image to be small;

using a Total Variation semi-norm;
using a Huber function.

23. The method of claim 16 wherein the optimization is solved using a convex programming solver.

24. At least one non-transitory computer-readable medium containing computer program instructions for correcting spatial artifacts within a composite radiographic image of an object, said instructions performing the steps of:
   generating the composite image by assembling a plurality of views of the object imaged by a radiographic scanner, wherein each view represents a different time, relative motion exists between the radiographic scanner and the object, and each view corresponds to a portion of data used to generate the composite image and where each view is no more than two pixels wide in a horizontal direction and many pixels tall in a vertical direction to cover entire height of the object;
   estimating a correctional shift profile comprising tailored correctional shifts to be applied to at least two of the views;
   correcting the views using the corresponding correctional shifts; and
   re-generating the image by assembling the corrected views.

25. Apparatus for correcting spatial artifacts within a composite radiographic image of an object, said apparatus comprising:
   a radiographic image scanner adapted to produce a plurality of views of the object, wherein each view represents a different time, relative motion exists between the radiographic scanner and the object, and each view corresponds to a portion of data used to generate the composite image and where each view is no more than two pixels wide in a horizontal direction and many pixels tall in a vertical direction to cover entire height of the object;
   coupled to the radiographic image scanner, means for estimating a correctional shift profile comprising tailored correctional shifts to be applied to at least two of the views;
   coupled to the estimating means, means for correcting the views using the corresponding correctional shifts; and
   coupled to the correcting means, means for assembling the corrected views to form a corrected image.

26. The apparatus of claim 25 wherein the estimating means includes an optimization algorithm that is applied to find the shift profile that minimizes a sum of a set of penalty functions such that the optimization algorithm at least approximately satisfies a set of hard constraints.

* * * * *